(12) United States Patent
Weimann

(10) Patent No.: US 10,588,869 B2
(45) Date of Patent: *Mar. 17, 2020

(54) DEVICE AND METHOD FOR THE TRANSDERMAL DELIVERY OF CANNABIDIOL

(71) Applicant: LIFE TECH GLOBAL, LLC, Irvine, CA (US)

(72) Inventor: Ludwig Weimann, San Diego, CA (US)

(73) Assignee: Life Tech Global, LLC, Irvine, CA (US)

( * ) Notice: Subject to any disclaimer, the term of this patent is extended or adjusted under 35 U.S.C. 154(b) by 44 days.

This patent is subject to a terminal disclaimer.

(21) Appl. No.: 15/972,868

(22) Filed: May 7, 2018

(65) Prior Publication Data
US 2018/0333369 A1  Nov. 22, 2018

Related U.S. Application Data

(62) Division of application No. 15/172,365, filed on Jun. 3, 2016, now Pat. No. 9,962,340.

(60) Provisional application No. 62/172,920, filed on Jun. 9, 2015.

(51) Int. Cl.
A61K 9/70 (2006.01)
A61K 31/05 (2006.01)

(52) U.S. Cl.
CPC ............ A61K 31/05 (2013.01); A61K 9/7084 (2013.01)

(58) Field of Classification Search
CPC ............... A61K 31/05; A61K 9/7084
See application file for complete search history.

(56) References Cited

U.S. PATENT DOCUMENTS

| 4,309,520 | A  | * | 1/1982  | Blizzard    | C09J 183/02 525/477 |
| 8,435,556 | B2 | * | 5/2013  | Stinchcomb  | A61K 9/0014 424/443 |
| 8,513,323 | B2 | * | 8/2013  | Zhou        | B32B 27/06 523/105 |
| 2008/0233180 | A1 | * | 9/2008  | Zeltman     | A61K 9/7061 424/449 |
| 2009/0232887 | A1 | * | 9/2009  | Odidi       | A61K 9/06 424/457 |
| 2014/0100249 | A1 | * | 4/2014  | Sears       | A61K 31/137 514/325 |
| 2017/0071870 | A1 | * | 3/2017  | Weimann     | A61K 9/7053 |

* cited by examiner

Primary Examiner — Aradhana Sasan
Assistant Examiner — Quanglong N Truong
(74) Attorney, Agent, or Firm — Patnstr® APC; Tom Brody; Peter Jon Gluck, Esq.

(57) ABSTRACT

Transdermal delivery devices for the delivery of cannabidiol (CBD) are shown and described. In a reservoir-patch design, a microporous, hydrophilic membrane and a backing define a reservoir that houses a mixture of CBD, a polar liquid, and a gelling agent. The hydrophilic membrane is coated with an amine-compatible silicone skin adhesive. In a monolithic design, a release liner is coated with a mixture of CBD and a PIB or amine-compatible silicone skin adhesive laminated to the hacking material. In either design, the CBD may be provided as a pure compound or as a component of a cannabis oil.

8 Claims, 4 Drawing Sheets

DEVICE AND METHOD FOR THE TRANSDERMAL DELIVERY OF CANNABIDIOL

CROSS-REFERENCE TO RELATED APPLICATIONS

This application is a Divisional of U.S. patent application Ser. No 15/172,365, filed Jun. 3, 2016, which claims the benefit of U.S. Provisional Patent Application No. 62/172,920, filed Jun. 9, 2015, the entirety of which is hereby incorporated by reference.

BACKGROUND

Cannabidiol (CBD, C21H3002, CAS Registry No. 13956-29-1) is an active cannabinoid present in *Cannabis*, a genus of flowering plants that includes *Cannabis sativa, Cannabis indica*, and *Cannabis ruderalis*. Other cannabinoids include tetrahydrocannabinol (THC), tetrahydrocannabinolic acid (THC-a), cannabinol (CBN), and cannabichromene (CBC).

CBD and THC-a are main components of the marijuana plant. For decades, the CBD content in marijuana plants was very low (below 5%), and all efforts were directed toward increasing the content of psychoactive component of marijuana—THC—for recreational purposes. Recently however, extensive medical research of medicinal attributes of marijuana suggests that CBD is the most important a non-psychoactive component of marijuana that possesses a wide range of therapeutic benefits.

Growers of marijuana developed new strands of the plant with high content of CBD. When subjected to an extraction process the yield of CBD in the concentrated extract (oil, shatters) may approach 70% by weight and higher. The increased CBD concentration made it possible to formulate products consumed as edibles, tinctures capsules, lotions, and creams containing medicinal quantities of CBD. The CBD in such products has been used for serious therapeutic medical treatments such as: reversing alcohol induced brain damage, treating of severe social anxiety, turning off the cancer gene found in metastasis, effectively treating schizophrenia and epilepsy, treating neurogenerative disorders or even slowing down Parkinson's disease and Alzheimer's disease.

Successful use of CBS for medical treatments such as the foregoing depends on the dose of the medicine, reducing side effects, and patient compliance. Orally taken CBD is exposed to the gastric environment and liver, which metabolizes the medicine and thereby lowers its bioavailability. Creams and lotions act for a short time being rubbed off by cloth and washed off Transdermal delivery is an alternate route for delivering potent medicines. It circumvents the gastric system, and therefore, the medical substance does not cause liver damage and has increased bioavailability. In particular, children are most susceptible to such damage and may particularly benefit from the transdermal delivery of CBD because transdermal delivery allows for the controlled, sustained delivery of CBD to the body for at least 24 hrs—and possibly for 2-3 days—without damaging young livers.

Transdermal delivery of cannabinoids has been proposed. However, known reservoir-style transdermal devices have used liquid carriers and/or hydrophobic rate-controlling membranes and carriers which have undesirably limited the rate of mass transfer of CBD through the skin. In addition, certain known reservoir-style devices require an additional adhesive coated overlay to hold the device in place on the wearer's skin.

Monolithic transdermal devices (also known as "drug-in-adhesive" devices) for delivering cannabinoids have also been proposed. However, the adhesive used in such known devices has typically limited the rate of mass transfer of CBD to the skin.

Thus, a need has arisen for a transdermal device for delivering CBD.

DETAILED DESCRIPTION

Figure 1:
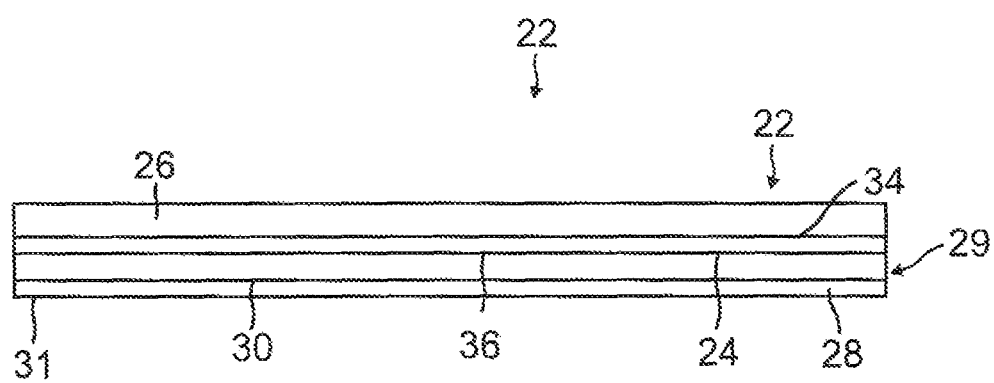
FIG. 1 is a side cross-sectional view of a reservoir-style transdermal device for delivering CBD to a wearer's skin.

The disclosure provides a transdermal patch formulation with CBD in PIB adhesive, from 1% to 30% and Vitamin C Palmitate. The disclosure also provides a device for transdermal delivery of cannabidiol (CBD), comprising a backing; a mixture of an adhesive and a therapeutically effective amount of cannabidiol coating on the backing, wherein the mixture includes at least one of tetrahydrocannabinol (THC), tetrahydrocannabinolic acid (THC-a), cannabinol (CBN), and cannabichromene (CBC), vitamin B12, Terpenes and Beta-carylophenol; wherein the adhesive comprises an amine-compatible silicone adhesive and the mixture has a first surface adhered to the backing and a second, skin-adhering surface, a release liner removably attached to the second, skin adhering surface of the mixture. In another aspect, the disclosure provides above transdermal reservoir patch wherein Vitamin B12 is delivered in the presence of at least one moiety selected from the group of THC, CBD and Terpenes. Also provided is transdermal reservoir patch further comprising Vitamin C Palmitate.

Described below are examples of transdermal delivery devices for delivering CBD through the epidermis of a wearer of the device. Both reservoir-style, and monolithic-style devices are described. In the reservoir style device, a reservoir comprising a solution of CBD (which may be present as substantially pure CBD or an oil extract of a cannabis plant which comprises CBD and other cannabinoids) and a liquid carrier is provided and is defined between a hydrophilic, porous membrane and a backing. One side of the hydrophilic, porous backing is coated with a skin adhesive that is covered with a release liner. To use the device, the user removes the release liner and contacts the skin adhesive-side of the membrane with the skin to affix the device to the body. Preferred skin adhesives include amine-compatible, silicone adhesives. The phrase "amine-compatible" refers to the fact that the adhesive is substantially non-reactive with amines. Many drugs are amines that bond with hydrogen donors. Silicone adhesive polymers typically have OH groups that are hydrogen donors. When mixed with drugs that have NH groups (amines) or OH groups (like cannabidiol) that can accept hydrogen, the drug and silicone polymer will bond through hydrogen bonding, which retards the diffusion of drug molecules from the adhesive matrix. To avoid that diffusion retardation, the OH groups of the silicone polymer, are capped with methyl groups. Such silicone adhesive will be called "amine compatible" which means they are essentially chemically neutral.

The CBD diffuses through the hydrophilic porous membrane and the skin adhesive and into the user's skin.

In a first monolithic-style device, a skin adhesive is mixed with the CBD (which may be present as substantially pure CBD or an oil extract of a cannabis plant which comprises CBD and other cannabinoids) to define a substantially monolithic mixture of adhesive and CBD. The skin adhesive is coated on a backing that is preferably occlusive. The skin adhesive is preferably an amine-compatible silicone adhesive.

In a second monolithic-style device, a skin adhesive is mixed with the CBD (which may be present as substantially pure CBD or an oil extract of a cannabis plant which comprises CBD and other cannabinoids) to define a substantially monolithic mixture of adhesive and CBD. The skin adhesive is preferably a polyisobutylene adhesive having a viscosity-average molecular weight ranging from about 30,000 Daltons to about 70,000 Daltons, preferably, from about 35,000 Daltons to about 65,000 Daltons, and more preferably from about 40,000 Daltons to about 60,000 Daltons.

Referring to FIG. 1, a reservoir-style transdermal delivery device 20 for the transdermal delivery of CBD is depicted. Reservoir-style transdermal delivery device 20 comprises a backing 22 and a hydrophilic, porous membrane 24. The backing 22 and hydrophilic, porous membrane 24 are attached to one another so as to define a closed volume which acts as a reservoir 26. A preparation 27 comprising CBD, a liquid carrier, and a gelling agent is disposed in the reservoir 26. First side 34 of the hydrophilic, porous membrane 24 is in contact with the preparation 27. A second side 36 of the hydrophilic, porous membrane 24 faces away from backing 22 and is coated with a skin adhesive 30. The skin adhesive 30 is preferably formulated to adhere the device 20 to the user's skin for a period of no less than about 24 hour's while avoiding appreciable skin irritation to the user's skin. Preferred skin adhesives 30 include amine-compatible, silicone, pressure sensitive adhesives. In certain examples, an amine-compatible silicone skin adhesive 30 is provided which comprises a trimethylsiloxy end-capped reaction product of a silanol end-blocked polydimethylsiloxane and a silicate resin. The skin adhesive is preferably provided as an organic solvent solution comprising from about 50 percent to about 70 percent by weight of solid adhesive in an organic solvent like heptane or ethyl acetate and having a viscosity at 20° C. of from about 400 mPa-s to about 1300 mPa-s, preferably from about 450 mPa-s to about 1250 mPa-s, and more preferably from about 500 mPa-s to about 1200 mPa-s.

A first surface 29 of a release liner 28 is releasably adhered to skin adhesive 30, and a second surface 31 of release liner 28 faces away from skin adhesive 30. Suitable release liners include occlusive polymeric films, such as polyester, polypropylene, coated with a release coating that is releasably adherable to silicone, polyisobutylene, and silicone adhesives. Suitable release coatings on first surface 29 of release liner 28 include fluoropolymers and silicone polymers. Commercially-available, coated release liners that are suitable for use as release liner 28 include Scotchpak 1022, 9741, 9744, 9748, and 9755 supplied by 3M of Minneapolis, Minn., and FRA 314 and 315 supplied by Fox River Co. To use the reservoir transdermal device 20, release liner 28 is peeled away from skin adhesive 30, thereby exposing skin adhesive 30, and the device 20 is applied so that the skin adhesive 30 contacts the user's skin.

Suitable examples of such amine-compatible silicone adhesives include the BIO-PSA 7-4301 and 7-4302 skin adhesives supplied by Dow Corning. BIO-PSA 7-4301 is a high tack, amine-compatible silicone adhesive in heptane available with a solids content of 60 percent and 70 percent and corresponding viscosities at 20° C. of 450 mPa-s and 1600 mPa-s. BIO-PSA 7-4302 is a high tack, amine-compatible silicone adhesive in ethyl acetate with a solids content of 60 percent by weight and a viscosity of 1200 mPa-s at 20° C. The skin adhesive 30 is coated to a thickness per unit area on the membrane 24 that is preferably from about 10 to about 20 g/m$^2$, more preferably from about 12-18 g/m$^2$, and still more preferably from about 14-16 g/m$^2$.

Hydrophilic, porous membrane 24 preferably has a mean flow pore size of no more than about 1 micron, preferably not more than about 0.8 microns, still more preferably no more than about 0.4 microns, and even more preferably no more than about 0.2 microns. At the same time, porous membrane 24 preferably has a mean flow pore size of no less than about 0.02 microns, more preferably no less than about 0.04 microns, still more preferably no less than about 0.06 microns, and even more preferably no less than about 0.08 microns. The mean flow pore size may be determined in accordance with the method set forth at page 17, line 22 to page 18, line 4 of published PCT Application WO2010072233, the entirety of which is hereby incorporated by reference.

In the same or other examples, hydrophilic porous membrane 24 preferably has a porosity of at least about 60 percent, more preferably at least about 65 percent, and still more preferably at least about 70 percent. At the same time, hydrophilic porous membrane 24 preferably has a porosity of no more than about 90 percent, more preferably no more than about 85 percent, and still more preferably no more than about 80 percent. Porosity values may be calculated as described at page 7, lines 24 to 27 of WO2010072233.

In the same or other examples, hydrophilic porous membrane 24 preferably has a thickness of no more than about 50 microns, preferably no more than about 40 microns, and even more preferably no more than about 35 microns. At the same time, hydrophilic porous membrane 24 preferably has a thickness of no less than about 10 microns, more preferably no less than about 20 microns, and still more preferably no less than about 25 microns. Membrane thicknesses may be determined as described at page 18, lines 19-21 of WO2010072233.

In the same or other examples, hydrophilic porous membrane 24 preferably has an air permeability as determined by the Gurley Test Method (according to ISO 5636-5) that is preferably at least about 10 sec/50 ml, more preferably at least about 20 sec/50 ml, and still more preferably at least about 25 sec/50 ml. At the same time, hydrophilic porous membrane 24 preferably has an air permeability of no more than about 50 sec/50 ml, more preferably no more than about 40 sec/50 ml, and still more preferably no more than about 35 sec/50 ml.

In the same or other examples, hydrophilic porous membrane 24 preferably has a tensile strength in the machine direction as determined by ASTM D882-12 that is preferably at least about 10 MPa, more preferably at least about 15 MPa, and still more preferably at least about 20 MPa. In the same or other examples, the hydrophilic porous membrane 24 preferably has a percent elongation in the machine direction as determined by ASTM D882-12 that is preferably at least about 10 percent, more preferably at least about 15 percent, and still more preferably at least about 20 percent.

Hydrophilic porous membrane 24 preferably comprises at least one polymeric material. In one example, hydrophilic porous membrane 24 comprises a polyolefin polymer and a hydrophilic component that comprises a hydrophilic polymer and optionally, a surfactant. As used herein, the term "hydrophilic" when used to describe a porous membrane refers to a membrane that at 20° C. provides a water flux for demineralized water through the membrane of at least 0.5 liters/(m$^2$ hbar).

The content of the polyolefin polymer is preferably less than or equal to 98 percent by weight based on the total dry weight of the membrane 24, and the content of the hydrophilic component(s) is preferably at least 2 weight percent based on the total dry weight of the membrane. In certain preferred examples, the membrane is formed by combining the polyolefin polymer with the hydrophilic components(s) and optional additives with a solvent to form a blend in the form of a gel, a solution, or a homogeneous mixture, followed by extruding the blend. Suitable polyolefins (such as polyethylene), hydrophilic components, and additives are described in WO2010072233.

One example of a commercially available hydrophilic, porous membrane that is suitable for use as hydrophilic, porous membrane 24 is supplied by Lydall Performance Materials B.V. under the name Evopor™ 5E02A. Evopor™ 5E02A is a porous hydrophilic membrane comprising a polyethylene support and a poly (ethyl vinyl) alcohol hydrophilic component.

As mentioned previously, preparation 27 comprises CBD and a liquid carrier. In certain examples, the polar organic liquid comprises a molecule having one or more carboxylic acid groups. In the same or other examples, the polar organic liquid comprises a molecule having one or more hydroxyl groups. Suitable polar organic liquids comprising one or more hydroxyl groups include those comprising between 2 and 30 carbon atoms per molecule, including without limitation, ethanol. Suitable polar organic liquids comprising one or more carboxylic acid groups include fatty acids, including without limitation oleic acid. Liquid carriers comprising ethanol and/or oleic acid are preferred, and liquid carriers comprising oleic acid are especially preferred. Suitable liquid carriers also include mixtures of polar organic liquids and water. Examples of such mixtures include mixtures of ethanol and water. In ethanol/water mixtures, the maximum concentration of water is preferably about ten (10) percent by weight of the total amount of ethanol and water.

Preparation 27 also may comprises a gelling agent which makes the preparation thixotropic. Suitable gelling agents include: sodium carboxymethyl cellulose, hydroxypropyl cellulose, hydroxyethyl cellulose, polyacrylic acid, methyl cellulose, xantam gum, etc. In certain examples, cellulose gelling agents such as hydroxyethylcellulose are preferred. The gelling agent increases the viscosity of and provides structural integrity to preparation 27, which improves the ease of placing and retaining preparation 27 in reservoir 26 before the reservoir 26 is closed by heat sealing the hydrophilic, porous membrane 24 to the occlusive backing 22. The gelling agent is preferably pharmacologically inactive.

The CBD is present in a therapeutically effective amount in preparation 27. A "therapeutically effective amount" is an amount of CBD sufficient to achieve a desired therapeutic effect over a desired time period. The CBD may be provided as substantially pure CBD, such as in a powder form, or as part of an oil extract comprising other cannabinoids. Presently (2015) marijuana growers extract CBD from plants in form of oils or "shatters" that have content of CBD ranging from 25 to 80% by weight of the oil and THC from 10-25 by weight of the oil. Recently, however, due to availability of sophisticated separators, it made possible to obtain pure CBD of 99.9% from hybrid marijuana plants or hemp plants with very low content of THC below 0.1%.

In certain examples, preparation 27 preferably comprises from about one (1) percent to about fifty (50) percent by weight CBD, more-preferably from about five (5) to about 30 percent by weight CBD, and more preferably from about 10 to about 20 percent by weight CBD.

In the same or other examples, the preparation 27 comprises a liquid carrier in amounts ranging from about 50 percent to about 99 percent by weight of the preparation 27. Preparation 27 also comprises from about one (1) percent to about ten (10) percent, and preferably about three (3) percent of a gelling agent (preferably hydroxyl propyl cellulose) by weight of the preparation 27. Preparation 27 also includes from zero to about ten (10) percent by weight of at least one penetration enhancer. In certain examples, the liquid carrier comprises at least one polar liquid of the type described previously. Suitable penetration enhancers include 1,2 propylene glycol, dimethyl sulfoxide (DMSO), oleic acid, and isopropyl palmitate (IPP).

When provided as substantially pure CBD, the amount of CBD in preparation 27 by weight of CBD plus liquid carrier(s) (i.e., excluding gelling agents such as cellulose derivatives like hydroxyl propyl cellulose), preferably ranges from about two (2) percent to about 40 percent by weight of the combination of CBD and liquid carrier(s) more preferably from four (4) percent to about 30 percent by weight of the combination of CBD and liquid carrier(s), and still more preferably from about five (5) percent to about 20 percent by weight of the combination of CBD and liquid carrier(s). When CBD is provided as part of a cannabis plant oil extract, the concentration of oil in the combination of oil and liquid carrier(s) is preferably from about five (5) percent to about, fifteen (15) percent by weight of the combination of oil and liquid carrier(s), more preferably from about eight (8) percent to about thirteen (13) percent by weight of the combination of oil and liquid carrier(s), and still more preferably from about nine (9) to about eleven (11) percent by weight of the combination of oil and liquid carriers(s). Ten percent oil by weight of the combination of oil and liquid carrier(s) is especially preferred.

Suitable backing materials for backing 22 include occlusive polymeric films such as polyethylene, polyethylene terephthalate (PET) and combinations thereof. Although device 20 may include an overlay patch, in preferred examples, one is not provided. In general, an overlay patch is not necessary if the hydrophilic, porous membrane 24 is already coated with skin adhesive 30. If the membrane 24 is not coated with an adhesive (e.g., in order to maximize the flux of CBD into the skin), an overlay patch should be placed over the reservoir 26 in order to ensure intimate contact of the hydrophilic, porous membrane 24 with skin. In certain examples, the skin contact area ("active transdermal flux area") of the membrane 24 of a device 20 is preferably at least about 10 cm$^2$, more preferably at least about 20 cm$^2$ and still more preferably at least about 30 cm$^2$. At the same time, the skin contact area of device 20 is preferably no more than about 30 cm$^2$, preferably no more than about 25 cm$^2$ and still more preferably no more than about 22 cm$^2$. At a given flux rate, the skin contact area may be selected to achieve the desired daily dose of CBD (or the dose over whatever time period is of therapeutic interest).

Figure 2:
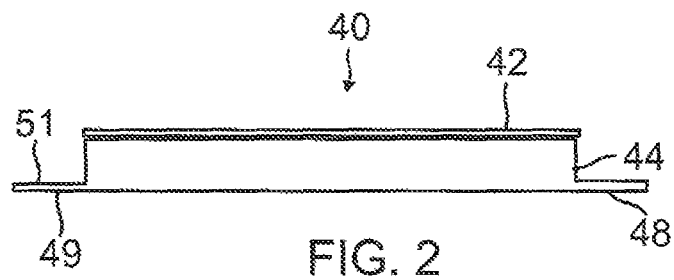
FIG. 2 is a side cross-sectional view of a monolithic-style transdermal device for delivering CBD to a wearer's skin.

Referring to FIG. 2, an example of monolithic-style transdermal drug delivery device 40 for delivering CBD is depicted. Monolithic transdermal device 40 includes a backing 42 of the type described previously with respect to backing 22 of reservoir transdermal device 20. A matrix 44 of skin adhesive mixed with a therapeutically effective amount of CBD is coated on one side of backing 42. The matrix 44 is preferably formulated to adhere the device 20 to the user's skin for a period of no less than about 24 hours while avoiding appreciable skin irritation to the user's skin. A release liner 48 is releasably adhered to matrix 44 on a surface of matrix 44 opposite the surface adhered to backing 42. First side 49 of release liner 48 faces away from matrix 44 and a portion of second side 51 of release liner 48 is adhered to matrix 44. To use the monolithic transdermal device 40, the release liner 48 is peeled away and the exposed surface of adhesive matrix 44 is applied to the skin.

The skin adhesive comprising matrix 44 preferably comprises at least one of an acrylate pressure sensitive adhesive, a polyisobutylene pressure sensitive adhesive, and an amine-compatible silicone pressure sensitive adhesive. Suitable acrylate adhesives include DuroTak 87-2516. Suitable polyisobutylene adhesives include those having a viscosity-average molecular weight ranging from about 30,000 Daltons to about 70,000 Daltons, preferably from about 35,000 Daltons to about 65,000 Daltons, and more preferably from about 40,000 Daltons to about 60,000 Daltons. Suitable polyisobutylene adhesives also have a viscosity at 20° C. ranging from about 1000 mPa-s to about 3000 mPa-s.

In certain preferred examples, matrix 44 preferably comprise a polyisobutylene adhesive having a viscosity-average molecular weight as described above and an adhesion/viscosity modifier. The adhesion/viscosity modifier is preferably a mineral oil or silicone fluid present in an amount ranging from about one (1) to about ten (10) percent by weight of matrix 44, more preferably from about two (2) to about six (6) percent by weight of matrix 44, and still more preferably from about three (3) to about four (4) percent by weight of the matrix 44. Mineral oils that are suitable for use as the adhesion/viscosity modifier have a molecular weight ranging from 100 to about 1000 Daltons, more preferably from about 200 to about 600 Daltons, even more preferably from about 350 Daltons to about 450 Daltons, and still more preferably about 400 Daltons. Silicone fluids that are suitable for use as the adhesion/viscosity modifier preferably comprise —OH end-capped polydimethylsiloxanes having a kinematic viscosity at 20° C. ranging from about 100 cSt to about 1000 cSt. Commercially available silicone fluids that may be used as the adhesion/viscosity modifier include the Dow Corning Q7-9120 fluids, which are available in kinematic viscosities (at 20° C.) of 20, 100, 350, 1000, and 12,500 cSt. In preferred examples of silicone adhesion/viscosity modifier, the Q7-9120 100 cSt or 1000 cSt for mixtures thereof) are used.

Preferred polyisobutylene adhesives are not supplied with mineral oil. In certain preferred examples, the polyisobutylene component of matrix 44 is a Vistanex LM polyisobutylene adhesive. In other preferred examples, the polyisobutylene component of matrix 44 is an Oppanol B13 polyisobutylene adhesive supplied by BASF.

In yet another example, the adhesive component of matrix 44 may comprise a blend of acrylic adhesive and polyisobutylene adhesive, and preferably, a blend of an acrylic adhesive and a polyisobutylene adhesive having the viscosity-average molecular weight described above (from about 30,000 Daltons to about 70,000 Daltons, preferably from about 35,000 Daltons to about 65,000 Daltons, and more preferably from about 40,000 Daltons to about 60,000 Daltons). When acrylic adhesives are combined with such polyisobutylene adhesives, the amount of acrylic adhesive by weight of the total amount of adhesive in matrix 44 is preferably from about one (1) to about 50 percent. In one example, the adhesive component of matrix 44 comprises 80 percent Oppanol B13 by weight of the total amount of adhesive in matrix 44 and twenty (20) percent Durotak 87-2516 by weight of the total amount of adhesive in matrix 44.

In examples in which matrix 44 comprises an amine-compatible silicone adhesive, the amine-compatible silicone adhesive is preferably of the type described previously with respect to skin adhesive 30 of reservoir transdermal device 20.

The amount of CBD in the matrix 44 preferably ranges from about one (1) to about 30 percent by weight of the matrix 44, more preferably from about two (2) percent to about 25 percent by weight of the matrix 44, and still more preferably from about five (5) percent to about twenty (20) percent by weight of the matrix 44. The amount of cannabis compounds other than CBD is preferably less than about one (1) percent. In those cases where pure CBD is used in matrix 44, the amount of pure CBD by weight of matrix 44 is preferably from about two (2) percent to about twenty (20) percent, more preferably from about four (4) percent to about fifteen (15) percent, and still more preferably from about five (5) percent to about ten (10) percent.

When CBD is provided as part of a cannabis plant oil extract, the amount of oil by weight of matrix 44 is preferably from about fifteen (15) percent to about 40 percent by weight, preferably from about twenty (20) percent to about 30 percent by weight, and still more preferably from about 24 percent to about 26 percent by weight in such cases, the CBD content as a percentage of the cannabis plant oil extract is preferably from about 25 percent to no more than about 50 percent, more preferably from about 30 percent to about 50 percent, and still more preferably from about 40 percent to about 50 percent by weight of the cannabis oil.

In certain preferred examples wherein CBD is provided as part of a cannabis plant oil extract, the oil further comprises rosins and/or terpenes that remain present after extraction. It has been found that these rosins and terpenes improve adhesion to the skin. Thus, the use of plant extract oils in monolithic device 40 provides a synergistic effect in both allowing for transdermal delivery of CBD and providing a device 40 that can withstand showers and minor brushings over the worn device 40 for many days.

Monolithic device 40 may also include penetration enhancers, including but not limited to oleic acid, isopropyl palmitate (IPP), DMSO, 1,2 propylene glycol, and isopropyl myristate (IPM). The amount of penetration enhancer preferably ranges from zero to about ten (10) percent by weight of the matrix 44.

In certain examples, the skin contact area of device 20 is preferably at least about 10 cm$^2$, more preferably at least about 15 cm$^2$, and still more preferably at least about 18 cm$^2$. At the same time, the skin contact area of device 20 is preferably no more than about 30 cm$^2$, preferably no more than about 25 cm$^2$ and still more preferably no more than about 22 cm$^2$. At a given flux rate, the skin contact area may be selected to achieve the desired daily dose of CBD (or the dose over whatever time period is of therapeutic interest).

EXAMPLE 1

The effects of using a hydrophobic, porous membrane versus a hydrophilic, porous membrane (such as membrane 24) in reservoir transdermal device 20 are studied in this example. A mixture is formed by dissolving CBD powder in ethanol to yield a solution comprising 10 percent by weight CBD and 90 percent by weight ethanol. The backing 22 is an occlusive backing film (PE/PET from 3M). Hydroxy ethyl cellulose is added to the solution to yield a thixotropic preparation 27. A volume of 300 μL of the preparation is placed in the reservoir 26.

The skin adhesive 30 is a BIO PSA 7-4301 adhesive coated to a thickness of 15 g/m$^2$ on side 36 of membrane 24. An overlay adhesive patch is placed over the reservoir which forms an island in the middle. The overlay assures adhesion of the reservoir to the skin. The device 20 is contacted with a human cadaver epidermis, and diffusion through the epidermis is measured using the Franz Diffusion Cell method.

Figure 3:
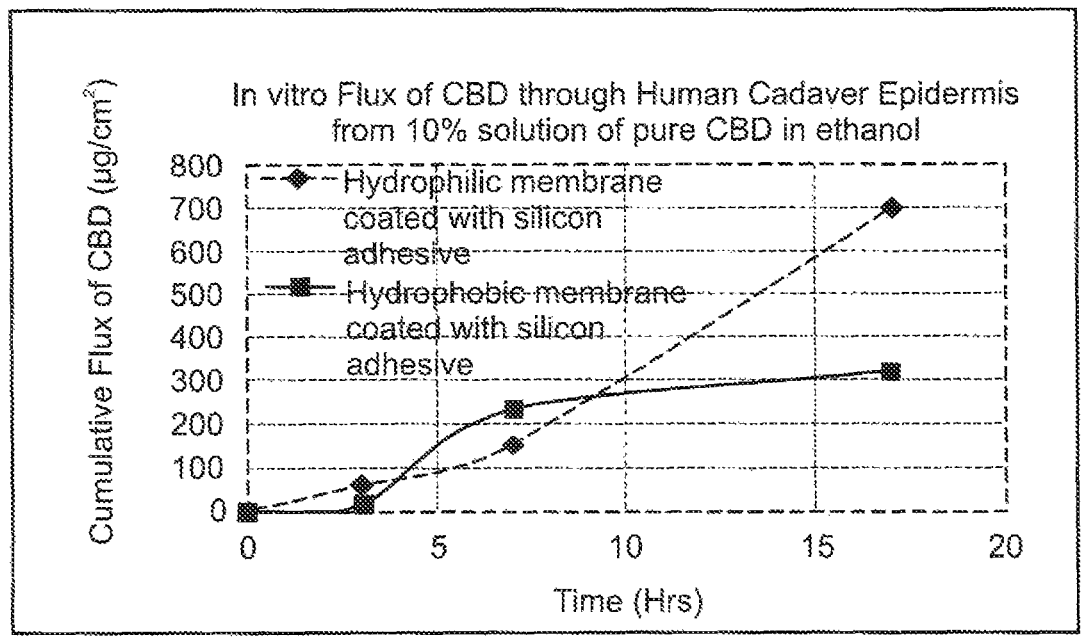
FIG. 3 is a graph depicting the cumulative flux (pg/cm$^2$) of CBD with respect to time (hours) through a human cadaver epidermis from a solution comprising ten (10) percent by weight CBD and 90 percent by weight of an ethanol solvent through each of a hydrophilic, microporous membrane and a hydrophobic, microporous membrane.

In a first run, membrane 24 is a Lydall® Evopor™ 5E02A, hydrophilic, microporous membrane (of 0.2 μm pore size). In a second run, the device 20 is constructed similarly, but membrane 24 is a hydrophobic Lydall® Solupor™ 7P03A porous membrane. As FIG. 3 indicates, after a period of about 9 hours, the device 20 with the hydrophilic membrane provides a monotonically increasing cumulative flux of CBD through the cadaver skin which significantly exceeds the cumulative flux of CBD from the hydrophobic membrane device, which becomes asymptotic at about 300 μg/cm$^2$.

EXAMPLE 2

The reservoir device 20 of Example 1 is used, but instead of using ethanol alone as the liquid carrier, a mixture of ethanol and water is used wherein the ethanol comprises 70 percent by weight of the ethanol/water mixture, and water comprises 30 percent by weight of the ethanol/water mixture. The amount of CBD by weight of the combination of CBD and ethanol/water is 5 percent, and the amount of ethanol/water is 91.5 percent. The gelling agent is hydroxyethylcellulose, which is present in an amount of about 3.5% by weight of the preparation 27. A first run is conducted in which the membrane is placed comprises CBD is present.

Figure 4:
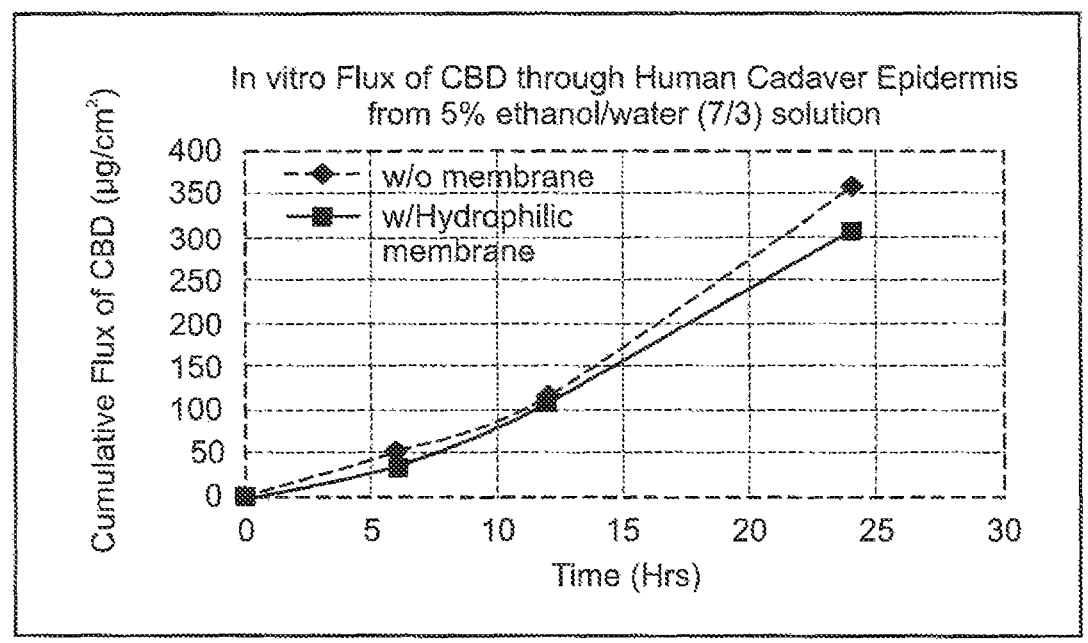
FIG. 4 is a graph depicting the cumulative flux ($\mu$g/cm$^2$) of CBD with respect to time (hours) through a human cadaver epidermis through a device with a hydrophilic, porous membrane and a device lacking such a membrane from a solution comprising five (5) percent by weight of CBD and 90 percent by weight of a solvent comprising 70 percent by weight ethanol and 30 percent by weight water.

The device 20 is contacted with a human cadaver epidermis, and diffusion through the epidermis is measured using the Franz Diffusion Cell method. In a first run, the hydrophilic, porous membrane 24 of Example 1 is used. In a second run, the membrane 24 is omitted so that CBD diffuses directly through the skin adhesive 30. The cumulative flux versus time is plotted in FIG. 4, which indicates that the permeability of CBD through the skin is the same regardless of whether the membrane 24 is provided. It is also discovered that an overlay patch (not shown in FIG. 1) is not required to hold device 20 on the skin.

EXAMPLE 3

This example is conducted using three reservoir transdermal devices such as those of Example 1, with each having the hydrophilic, porous membrane described therein. In each case, the preparation includes a mixture of CBD and a liquid carrier with ten (10) percent CBD by weight of the CBD/liquid carrier mixture. Three runs are conducted, each with a device that includes a different liquid carrier in its preparation 27: 1,2 propylene glycol, PEG-300, and oleic acid. Diffusion through a human cadaver epidermis is measured using the Franz Diffusion Method.

Figure 5:
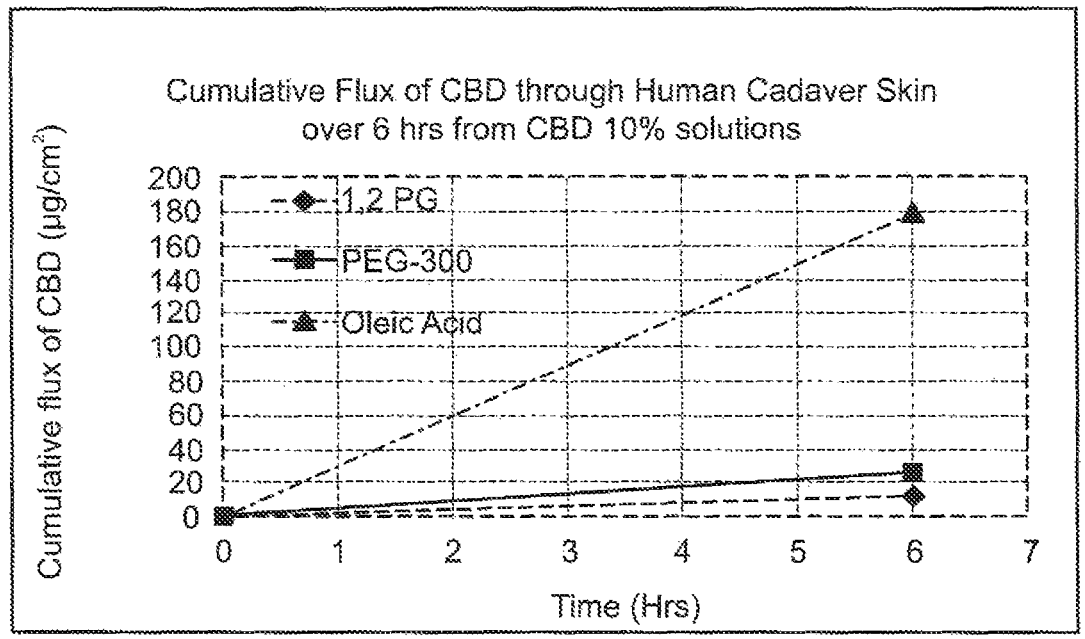
FIG. 5 is a graph depicting the cumulative flux ($\mu$g/cm$^2$) of CBD through a human cadaver epidermis over a six hour period from solutions comprising ten (10) percent by weight CBD and 90 percent by weight of one of three liquid carriers.

The cumulative flux versus time is plotted in FIG. 5. As the figure indicates, throughout the period, oleic acid provides a significantly better rate of transfer of CBD through the skin than either 1,2 propylene glycol or PEG-300.

EXAMPLE 4

Figure 6:
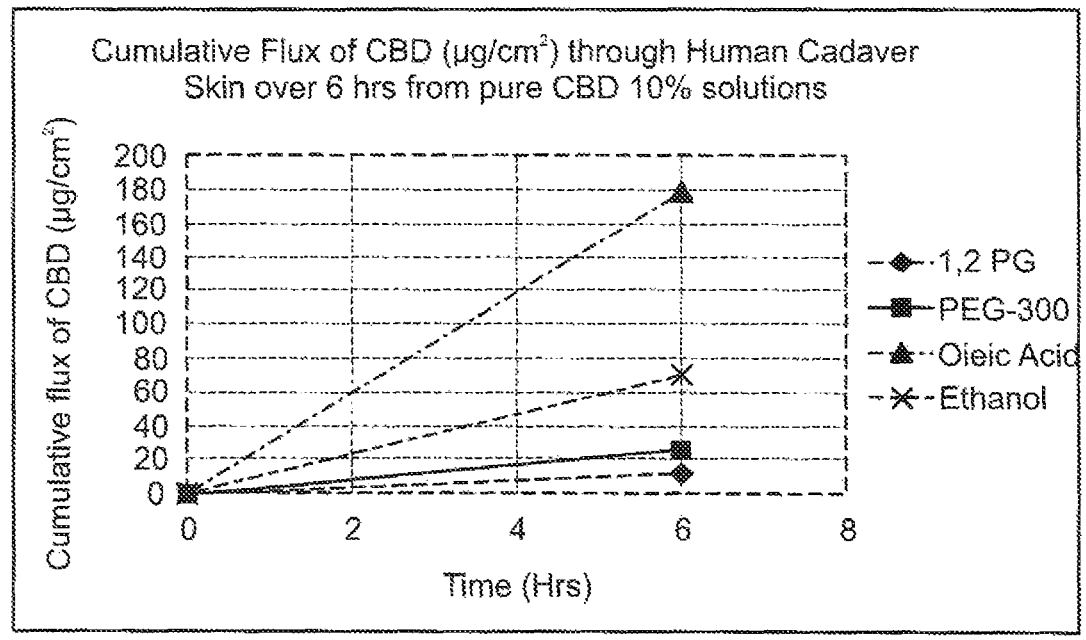
FIG. 6 is a graph depicting the cumulative flux ($\mu$g/cm$^2$) of CBD through a human cadaver epidermis over a six hour period from solutions comprising ten (10) percent by weight CBD and 90 percent by weight of one of four liquid carriers.

This example is similar to Example 3, except that an ethanol carrier is also tested. As indicated in FIG. 6, ethanol shows superior transfer of CBD through the skin relative to 1,2 propylene glycol and PEG-300. However, oleic acid provides superior transfer relative to all three of the other liquid carriers.

EXAMPLE 5

Figure 7:
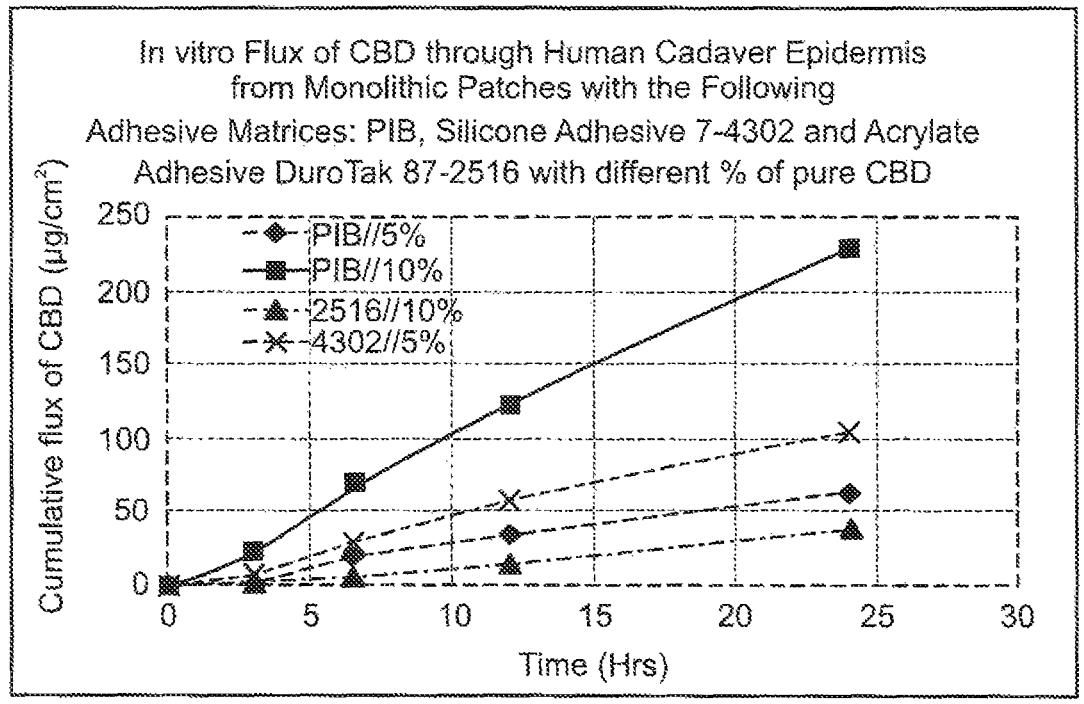
FIG. 7 is a graph depicting the cumulative flux ($\mu$g/cm$^2$) of CBD through a human cadaver epidermis from a monolithic adhesive matrix comprising varying amounts (weight percent) of three different adhesives and varying amounts (weight percent) of pure CBD.

A monolithic transdermal device 40 is constructed using a matrix 44 of pure CBD and three different adhesives. A first device 40 includes a PE/PET backing and a matrix 44 comprising 95 percent Vistanex LM polyisobutylene adhesive by weight of matrix 44 mixed with 5 percent substantially pure CBD by weight of matrix 44. A second device is similarly constructed, but the amount of CBD in the matrix 44 is 10 percent by weight of the matrix 44, and the amount of Vistanex LM is 90 percent by weight of the matrix 44. A third patch is constructed using a DuroTak 87-2516 adhesive in an amount of 90 percent by weight of matrix 44 and 10 percent CBD by weight of matrix 44, and a fourth patch is constructed using a BIO PSA 7-4302 adhesive in an amount of 95 percent by weight of matrix 44 and 5 percent CBD by weight of matrix 44. As indicated in FIG. 7, the Vistanex LM/10 percent CBD device provides superior CBD transfer through the epidermis relative to the three other devices.

EXAMPLE 6

Figure 8:
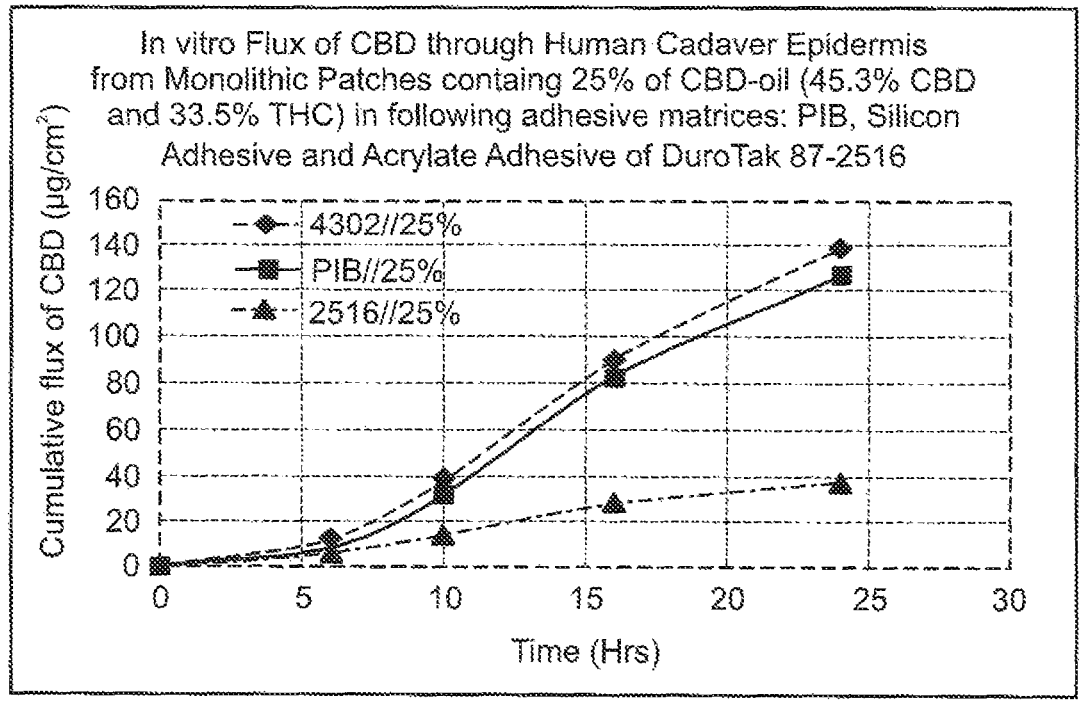
FIG. 8 is a graph depicting the cumulative flux ($\mu$g/cm$^2$) of CBD through a human cadaver epidermis from a monolithic adhesive matrix comprising varying amounts (weight percent) of three different adhesives and 25 percent by weight of a cannabis oil comprising 45.3 percent by weight CBD and 33.5 percent by weight THC.

Three monolithic devices are constructed similar to those of Example 5. However, instead of pure CBD, a cannabis extract oil comprising 45.3 percent CBD and 33.5% THC is mixed with the adhesive to form the adhesive matrix 44. In each device, the amount of oil in the matrix 44 is 25 percent by weight of the matrix 44. The matrix 44 in the first device comprises 75 percent by weight BIO PSA 7-4302. The matrix 44 in the second device comprises 75 percent by weight Vistanex LM, and the matrix 44 in the third device comprises 75 percent by weight DuroTak 87-2516. As indicated in FIG. 8, the devices with a PIB (Vistanex LM) and amine-compatible silicone adhesive (BIO PSA 7-4302) provide significantly superior CBD transfer through the skin as compared to the acrylate (DuroTak 87-2516) adhesive.

Notably, from a 20 cm$^2$ reservoir device using a liquid carrier comprising ethanol and a CBD concentration of 10 weight percent (where 20 cm$^2$ is the skin contact area), the expected daily dose of CBD is 30 mg, which is six times higher than the expected dose from a monolithic patch of the same skin contact area.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A device for the transdermal delivery of cannabidiol (CBD), comprising:
   a backing;
   a mixture of an adhesive and a therapeutically effective amount of cannabidiol coated on the backing, wherein the mixture includes at least one of an adhesive, cannabidiol, and tetrahydocannabinol (THC),
   wherein the adhesive comprises an amine-compatible silicone adhesive and the mixture has a first surface adhered to the backing and a second, skin-adhering surface;
   a release liner removably attached to the second, skin adhering surface of the mixture.

2. The device of claim 1, wherein the amine-compatible silicone adhesive comprises trimethylsiloxy and groups that are substantially non-reactive with amines.

3. The device of claim 1, wherein the amine-compatible silicone adhesive comprises a trimethylsiloxy end-capped reaction product of a silanol endblocked polydimethylsiloxane with a silicate resin.

4. The device of any of claim 1, wherein the adhesive has a viscosity ranging from about 1000 mPa-s to about 1800 mPa-s at a temperature of 20° C.

5. The device of claim 1, further comprising Vitamin B12, wherein Vitamin B12 is delivered in the presence of at least one moiety selected from the group of THC, CBD and terpenes.

6. The device of claim 1, further comprising at least one mechanism of CBD and THC delivery from liquid saturated matrix (EtOH+water); and use of hemp oil in delivering CBD from saturated alcohol solution, wherein the mechanism comprises a skin adhesive provided as an organic solvent solution comprising from about 50% to about 70% by weight of a solid adhesive in an organic solvent, having a viscosity at 20 degrees C. of from about 400 mPa-s to about 1300 mPa-s.

7. The device of claim 1, further comprising Vitamin C palmitate.

8. The device of claim 1, wherein the mixture comprises a cannabis plant oil extract.

* * * * *